(12) United States Patent
Walji et al.

(10) Patent No.: US 11,857,002 B2
(45) Date of Patent: Jan. 2, 2024

(54) SURGICAL GOWNS

(71) Applicant: Mayo Foundation for Medical Education and Research, Rochester, MN (US)

(72) Inventors: Salim M. Walji, Albuquerque, NM (US); Joseph A. Dearani, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 19 days.

(21) Appl. No.: 17/056,581

(22) PCT Filed: May 30, 2019

(86) PCT No.: PCT/US2019/034570
§ 371 (c)(1),
(2) Date: Nov. 18, 2020

(87) PCT Pub. No.: WO2019/232158
PCT Pub. Date: Dec. 5, 2019

(65) Prior Publication Data
US 2021/0204620 A1 Jul. 8, 2021

Related U.S. Application Data

(60) Provisional application No. 62/677,843, filed on May 30, 2018.

(51) Int. Cl.
*A41D 13/00* (2006.01)
*A41D 13/12* (2006.01)

(52) U.S. Cl.
CPC ..... *A41D 13/0012* (2013.01); *A41D 13/1209* (2013.01)

(58) Field of Classification Search
CPC ............ A41D 13/1209; A41D 13/0012; A41D 13/04; A41D 13/12; A41D 13/1236;
(Continued)

(56) References Cited

U.S. PATENT DOCUMENTS 2,066,072 A * 12/1936 Powell ............... A41D 13/0012
2/51
2,260,427 A * 10/1941 Bailey .................. A41D 15/002
2/94

(Continued)

FOREIGN PATENT DOCUMENTS

JP         2009-249759         10/2009

OTHER PUBLICATIONS

English language translation of JP 2009249759 (doc published Oct. 2009).*

(Continued)

*Primary Examiner* — Amy Vanatta
(74) *Attorney, Agent, or Firm* — Fish & Richardson P.C.

(57) ABSTRACT

Surgical gowns can be configured to be worn by a human and to be sterile for use in a sterile surgical environment. Such a sterile surgical gown can include one or more pockets attached to the gown and configured to store surgical instruments. The sterile surgical gown can also include one or more rings attached to the gown and configured to hold surgical instruments. In some embodiments, a patch that is attachable to the gown. The patch can include one or more additional pockets or additional rings.

20 Claims, 1 Drawing Sheet

(58) Field of Classification Search
CPC ............ A41D 13/1245; A41D 13/1263; A41D 13/1281; A41D 27/20; A41D 27/204; A41D 1/18; A41D 1/02; A41D 1/04; A41D 27/208; A41D 13/02; A41D 1/002; A41D 3/00; A41D 3/02; A41D 3/08; A61B 2050/301; A41B 1/02; A41B 1/18
USPC .............................................................. 2/94
See application file for complete search history.

(56) References Cited

U.S. PATENT DOCUMENTS

| | | | | |
|---|---|---|---|---|
| 2,785,409 | A * | 3/1957 | Lackey | A41D 13/0012 2/51 |
| 2,846,685 | A * | 8/1958 | Ehrich | A41D 13/0012 2/51 |
| 3,359,569 | A | 12/1967 | Rotanz et al. | |
| 4,637,075 | A * | 1/1987 | Ingrisano | A41D 13/12 2/253 |
| 4,791,681 | A * | 12/1988 | Dean | A41D 13/012 2/253 |
| 5,024,361 | A * | 6/1991 | Flowers | A45F 5/00 224/901.2 |
| 5,082,111 | A * | 1/1992 | Corbitt, Jr. | A61M 25/02 206/478 |
| 5,617,582 | A * | 4/1997 | Burwell | A41D 13/0012 2/119 |
| 5,652,961 | A * | 8/1997 | Knight-Yurt | A41D 13/12 2/114 |
| 6,308,875 | B1 | 10/2001 | Almo | |
| 10,478,177 | B2 * | 11/2019 | Gorek | A61B 42/10 |
| 2005/0188450 | A1 * | 9/2005 | Clark | A41D 13/1209 2/247 |
| 2010/0064408 | A1 * | 3/2010 | Kemper | A41D 13/1209 2/243.1 |
| 2012/0030851 | A1 * | 2/2012 | Kinder | A41D 13/1209 2/69 |
| 2014/0299739 | A1 | 10/2014 | Bradow | |
| 2015/0026862 | A1 * | 1/2015 | Silverberg | A41D 13/0058 2/243.1 |
| 2015/0296900 | A1 | 10/2015 | Huang et al. | |
| 2016/0135517 | A1 * | 5/2016 | Silverberg | A41D 13/005 2/93 |
| 2017/0332770 | A1 * | 11/2017 | Miner | H01F 7/0252 |
| 2021/0022421 | A1 * | 1/2021 | Mosler | A41D 27/208 |

OTHER PUBLICATIONS

PCT International Preliminary Report on Patentability in International Appln. No. PCT/US2019/034570, dated Dec. 1, 2020, 4 pages.

PCT International Search Report and Written Opinion in International Appln. No. PCT/US2019/034570, dated Aug. 7, 2019, 5 pages.

Sun-med.com [online], "Ethox Instrument Holder: Surgi-Kit® Sterile," upon information and belief, available no later than May 30, 2018, retrieved on May 13, 2021, retrieved from URL<https://sun-med.com/product/detail/surgikit>, 1 page.

Woolston, "Surgical Gown with Instrument Pockets," JAMA, 1941, 117(1):21.

* cited by examiner

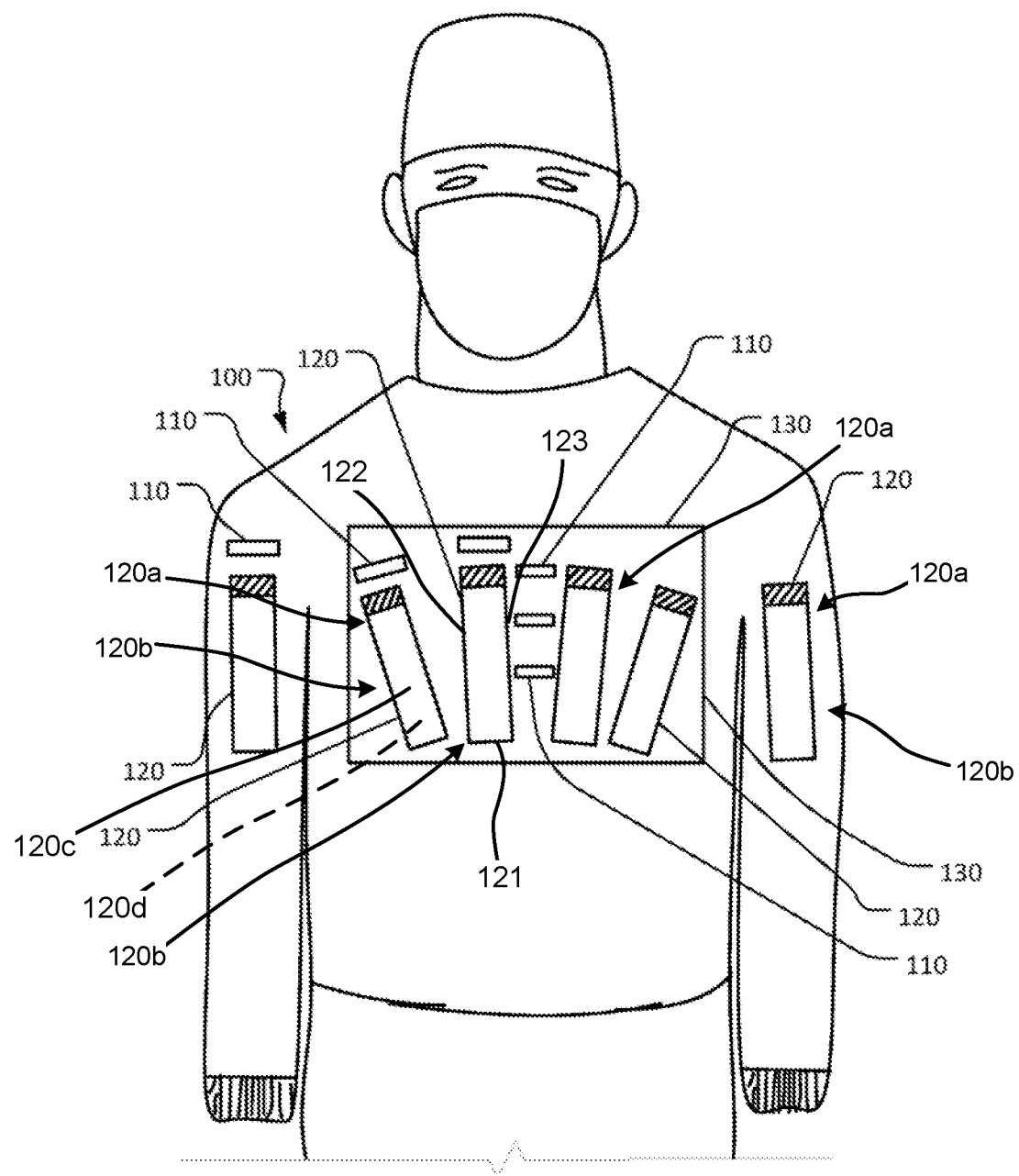

SURGICAL GOWNS

CROSS-REFERENCE TO RELATED APPLICATIONS

This application is a National Stage application under 35 U.S.C. § 371 of International Application No. PCT/US2019/034570, having an International Filing Date of May 30, 2019, which claims priority to U.S. Application Ser. No. 62/677,843, filed on May 30, 2018. The disclosure of the prior application is considered part of the disclosure of this application, and is incorporated in its entirety into this application.

BACKGROUND

1. Technical Field

This document relates to improved designs of surgical gowns.

2. Background Information

During surgery, the Certified Scrub Technician (CST) is generally focused on the needs of the Primary Surgeon ("Surgeon"), and is busy passing instruments to the Surgeon. The needs of the "Assistants" (Assistant Surgeon/Resident/Certified Surgical Assistant) on the other side of the surgical table are legitimate but sometimes can be a distraction from the CST's point of view. From the Assistant's point of view, any delay in getting the necessary instruments can sometimes be frustrating and hinder the smooth running of the procedure.

SUMMARY

This document describes improved designs of surgical gowns.

In one implementation, this disclosure is directed to a surgical gown configured to be worn by a human and to be sterile for use in a sterile surgical environment. Such a sterile surgical gown can include one or more pockets attached to the gown and configured to store surgical instruments. The sterile surgical gown can also include one or more rings attached to the gown and configured to hold surgical instruments. In some embodiments, a patch that is attachable to the gown. The patch can include one or more additional pockets or additional rings.

Particular embodiments of the subject matter described in this document can be implemented to realize one or more of the following advantages. In some embodiments, the surgical gowns described herein include pockets that can conveniently contain basic instruments such as scissors and forceps. These pockets can be located at different locations and varying angles to facilitate optimal access and thereby greatly obviate the need for almost 30-80% of the back and forth moves that occur between an Assistant and the CST.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1 is a schematic diagram of a clinician wearing an example surgical gown in accordance with some embodiments.

Like reference numbers represent corresponding parts throughout.

DETAILED DESCRIPTION

This document describes improved designs of surgical gowns.

A surgical gown 100 with some "pockets" as anchors (such as exemplified in FIG. 1), could provide literally a storage area that could provide the Assistants rapid access to their needs (forceps/scissors or such small items) and greatly obviate the need for almost 30-80% of the back and forth moves that occur between an Assistant and the CST. The inventors believe this would greatly improve the efficiency during a surgical procedure.

The inventive concepts and designs of the surgical gowns described herein may also have broader applicability in other areas of clinical and laboratory medicine as well as other industries beyond medicine—where convenience and improved efficiency are worthy and desired goals.

Referring to FIG. 1, the example surgical gown 100 can include one or more holsters, rings, and/or belt loops (collectively referred henceforth as "loops 110") and one or more pockets 120. In some embodiments, the loops 110 and/or the pockets 120 are both made of flexible material such as fabric.

The loops 110 and/or the pockets 120 are designed to hold instruments such as forceps/pickups and scissors or other simple, narrow instruments (the "instruments"). In some embodiments, these surgical gowns 100 are disposable—unlike the cloth gowns. In some embodiments, the gowns 100 can be reusable.

The size (width and length), position and angle of the pockets 120 and/or loops 110 can be selected as needed for optimal access, ease and sterility.

The loops 110 are somewhat similar in configuration as those on trousers that hold belts (belt loops). These can be in place of the pockets 120, or supplement the pockets 120 as additional guides and anchors for the instruments. The loops 110 can be made in various sizes. A single gown 100 can have loops 110 of various sizes. In some embodiments, the loops 110 are made of an elastic. In some embodiments, two or more loops 110 are arranged in alignment with each other so that a single instrument will be held by the two or more aligned loops 110.

In some embodiments, the pockets 120 can be free-standing by themselves or be supplemented with the loops 110, as mentioned above—or in various combinations. The goals of the pockets 120 and loops 110 are to hold the instruments and to promote easy and rapid access to the instruments for the surgeon and surgical assistants. This can greatly promote the surgical efficiency at multiple levels during a procedure for the entire surgical team.

The instruments are secured in a stable fashion, e.g., to prevent "floating" of the instruments in situations such as a leaning position. The tips of the instruments are kept protected as much as possible. Sterility is also safe-guarded. In some embodiments, the open tops of the pockets 120 can have a closure, such as a hook and loop closure, an elastic band, or a purse string.

The pockets 120 can be located at various locations on the gown 100. For example, one or more pockets can be located on the sleeves (above and/or below the elbow), bodice (upper torso area), sides, and/or legs of the gown 100.

The pockets 120 can have various shapes and may extend from a top portion 120a of each pocket to a bottom portion 120b of each pocket. In one aspect, each pocket may include a top portion 120c, which may form the outer portion or front of the pocket when the gown is in an in-use orientation and a bottom portion 120d which may form the inner portion or back of the pocket. In one aspect the bottom portion 120d may be directly connected to or part of the patch 130. Each pocket 120 may include pocket edges or a series of pocket borders or edges. The pocket borders or edges may include a right pocket border or edge 123, a left pocket border or edge 122, and a bottom pocket border or edge 121. The gown 100 can have pockets 120 with various shapes. Alternatively, in some embodiments all of the pockets 120 have the same shape on a gown 100. In some embodiments, one or more of the pockets 120 can be specifically shaped to contain a particular type of instrument. In some embodiments, the pocket 120 can comprise a mesh material, transparent material, and/or elastic material.

The pockets 120 and/or loops 110 can be attached directly on the gown 100 when the gown 100 is manufactured. Alternatively, or additionally, in some embodiments a separate patch 130 of fabric that includes one or more loops 110 and/or one or more pockets 120 can be attached to the gown 100 after the manufacturing of the gown 100. Such a separate, attachable patch 130 could be made in various shapes such as, but not limited to, square, rectangular, circular, and elliptical. An attachable patch 130 can be delivered together with the gown 100 as a system, or purchased/available separately from the gown 100.

The base material of the attachable patch 130 can have an adhesive back that could then be attached onto the gown 100 "on demand" in the O.R. as needed. As an alternative to adhesive attachment, in some embodiments the attachable patch 130 can be attached to the gown 100 using hook and loop fastener(s), zipper(s), ties, and the like, and combinations thereof. In some embodiments, the attachable patch 130 can come pre-secured and sealed to the gown 100 during manufacturing for greater weight-bearing security.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying FIGURES do not necessarily require the particular order shown, or sequential order, to achieve desirable results.

What is claimed is:

1. A surgical gown for holding surgical instruments, the surgical gown comprising:
a gown body with a first gown portion and a second gown portion, wherein the first gown portion is configured to be worn above a waist area of a user and the second gown portion is configured to be worn below the waist area of the user, wherein the first gown portion comprises:
an elongated first pocket with first pocket edges, the first pocket edges include a first pocket right side edge, a first pocket left side edge, a first pocket bottom edge, and having a length longer than a width and an opening along the width;
an elongated second pocket with second pocket edges separate from the first pocket edges, wherein the second pocket edges include a second pocket right side edge, a second pocket left side edge and a second pocket bottom edge, and wherein the second pocket has a length longer than a width and an opening along the width;
a loop; and
a base material,
wherein the first pocket is connected to the surgical gown via a first portion of the base material and the first portion of the base material extends directly from the opening of the first pocket,
wherein the second pocket is connected to the surgical gown via a second portion of the base material and the second portion of the base material extends directly from the opening of the second pocket, and
wherein the loop, the first pocket, and the second pocket are permanently connected to the grown and arranged in a fixed configuration in relation to one another and are configured to releasably hold surgical instruments.

2. The surgical gown of claim 1, wherein the base material includes an adhesive by which the base material is permanently connected to the surgical gown.

3. The surgical gown of claim 1, wherein the first pocket and the second pocket each have a top section and a bottom section and a distance between the top sections of the first and second pockets is less than a distance between the bottom sections of the first and second pockets.

4. The surgical gown of claim 1, wherein the loop is directly and permanently connected to the gown.

5. The surgical gown of claim 1, wherein the loop is between the first pocket and the second pocket.

6. The surgical gown of claim 1, wherein the loop is connected to the gown via the base material.

7. The surgical gown of claim 1, wherein the loop is directly connected to the gown.

8. A gown configured to be worn by a human for use in a surgical environment, the gown comprising:
  a gown body with a first gown portion and a second gown portion, wherein the first gown portion is configured to be worn above a waist area of a user and the second gown portion is configured to be worn below the waist area of the user, wherein the first gown portion comprises:
  a base material;
  a first pocket connected to the base material with three pocket borders;
  a second pocket connected to the base material, wherein the second pocket is angled relative to the first pocket and includes three pocket borders that are separate from the borders of the first pocket; and
  one or more rings
  wherein the first pocket is connected to the gown via a first portion of the base material and the first portion of the base material directly extends from an opening of the first pocket,
  wherein the second pocket is connected to the surgical gown via a second portion of the base material and the second portion of the base material directly extends from an opening of the second pocket, and
  wherein the one or more rings, the first pocket, and the second pocket are each configured to hold surgical instruments and are permanently connected to the gown.

9. The gown of claim 8, wherein the second pocket is attached to a chest area of the gown.

10. The gown of claim 9, wherein the one or more rings includes at least one ring attached to a sleeve of the gown and at least one ring attached to the chest area of the gown.

11. The gown of claim 8, wherein the one or more rings are loops of fabric connected to the gown via the base material.

12. The gown of claim 8, wherein the one or more rings are loops of fabric that are directly connected to the first portion of the gown.

13. The gown of claim 8, wherein the base material is a patch formed of a single piece of material.

14. A surgical gown comprising:
  a first portion configured to be worn above a waist area of a user; and
  a second portion configured to be worn below the waist area of the user,
  the first portion including a base material with:
  a first pocket with first pocket borders, the first pocket borders comprising a first pocket right side border, a first pocket left side border, a first pocket bottom border, wherein the base material extends from an opening of the first pocket;
  a second pocket with second pocket borders separate from the first pocket borders, wherein the second pocket borders comprises a second pocket right side border, a second pocket left side border and a second pocket bottom border, wherein the base material extends from an opening of the second pocket; and
  a loop,
  wherein the first pocket and the second pocket have openings and are arranged at a non-zero angle relative to each other, and
  wherein the first pocket and the second pocket each comprise a top section and a bottom section, wherein the bottom sections of the first pocket and the second pocket are each
  permanently connected to an outside facing surface of the surgical gown.

15. The surgical gown of claim 14, wherein the bottom sections of the first and second pockets are larger than the top sections of the first and second pockets.

16. The surgical gown of claim 14, wherein the top section and the bottom section of at least one of the first and second pockets are different materials.

17. The surgical gown of claim 14, wherein the bottom sections are larger than the top sections in directions extending past the openings of the first pocket and the second pocket.

18. The surgical gown of claim 14, wherein the loop is located between the first pocket and the second pocket.

19. The gown of claim 14, wherein the first pocket borders and second pocket borders are connected to the base material.

20. The gown of claim 14, wherein the first pocket and the second pocket are substantially symmetrical with respect to a vertical center-line of the gown.

* * * * *